United States Patent [19]

Daty et al.

[11] Patent Number: 4,649,116
[45] Date of Patent: Mar. 10, 1987

[54] MAGNETIC MEANS FOR WITHDRAWING MAGNETIC GEL BEADS FROM AN ASSAY FLUID

[75] Inventors: Jean Daty, La Chapelle en Serval; André Assimon, Argenteuil, both of France

[73] Assignee: Institut Pasteur, Paris, France

[21] Appl. No.: 666,263

[22] Filed: Oct. 29, 1984

[30] Foreign Application Priority Data

Oct. 27, 1983 [FR] France ................. 83 17166

[51] Int. Cl.⁴ ............................................. C12M 1/00
[52] U.S. Cl. .................. 435/287; 210/222; 294/65.5; 335/295
[58] Field of Search .............. 435/287; 294/65.5; 335/293, 295, 286, 285; 422/186.01; 210/222

[56] References Cited

U.S. PATENT DOCUMENTS

| 512,381 | 1/1854 | Keyes ........................... 335/285 X |
| 2,471,764 | 5/1949 | Miller et al. ................... 335/293 X |
| 3,985,649 | 10/1976 | Eddelman . |
| 4,272,510 | 6/1981 | Smith et al. . |

FOREIGN PATENT DOCUMENTS 2334106 5/1978 France .
2537725 12/1985 France .

OTHER PUBLICATIONS

Western Electric, Technical Digest No. 20, Oct. 1970, "Magnetic Handling Unit", p. 29.

Primary Examiner—Randall L. Green
Attorney, Agent, or Firm—Oblon, Fisher, Spivak, McClelland & Maier

[57] ABSTRACT

Magnetic device for withdrawing magnetic gel beads or the like from a biological fluid and transferring them to an immunoenzymatic assay medium. This device includes a housing of insulating material, particularly of plastic material, into which is inserted a magnet and over the height of which is formed a traversing orifice in which is housed a rod formed of a lower portion of magnetizable material and an upper portion of non-magnetizable material on which is mounted a return spring, between a stop washer fixed in the vicinity of the upper end of the rod and the upper surface of the housing. The device can advantageously be included in a ready-for-use kit for carrying out immunoenzymatic assays.

2 Claims, 3 Drawing Figures

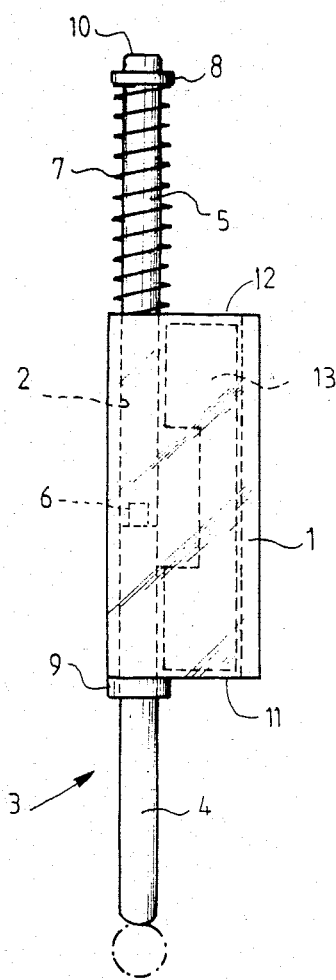
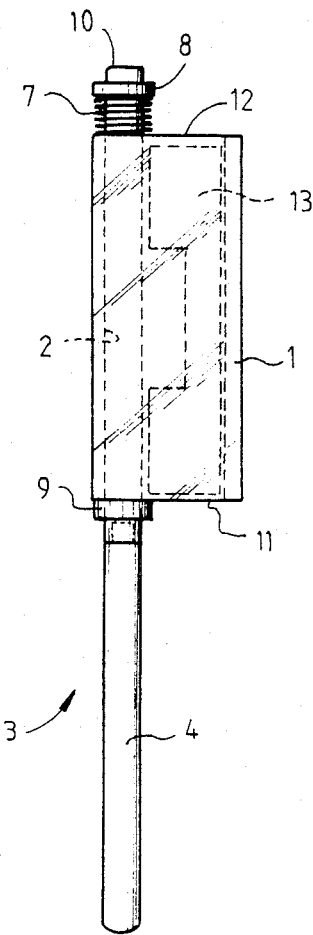
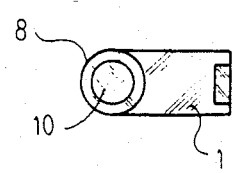

MAGNETIC MEANS FOR WITHDRAWING MAGNETIC GEL BEADS FROM AN ASSAY FLUID

BACKGROUND OF THE INVENTION

1. Field of the Invention

The present invention relates to improvements in or to magnetic means for withdrawing magnetic gel beads from a biological medium.

2. Description of the Background

Magnetic gels useful for immunoenzymatic assays are known through French Patent of INSTITUT PASTEUR No. 2 334 106. These magnetic gels are constituted by an acylamide and/or agarose gel containing magnetic particles, coupled with a protein such as an antibody or an antigen, through a suitable coupling agent, such as glutaraldehyde. They are used for carrying out the immunoenzymatic assay of the antigen or of the corresponding antibody contained in a biological liquid to be assayed. After incubation, the magnetic gel is separated in a first step, from the biological liquid and, in the second step, from the protein (antigen or antibody) marked by an immunoenzymatic assay enzyme, each time by applying a magnetic field outside the tube in which the assay takes place, to retain the magnetic gel on the wall of the tube.

French Pat. No. 2,537,725 uses specific antigenic anti-determinant antibodies, for the immunobacteriological detection of pathogenic germs possessing specific antigenic determinants, in contaminated biological media. In accordance with the process of detection which forms the subject of this patent, after incubation with the biological liquid supposed contaminated, the magnetic gel beads are withdrawn from the biological liquid by magnetic means, preferably constituted by a magnetizable rod, by means of which they are transferred to a gelosed medium on which the detection process is pursued. The magnetizable rod used for this purpose is a magnetizable rod coated with "Teflon".

It has however become apparent that such a magnetizable rod has the drawback on the one hand of being insufficiently isolated by the "Teflon" coating and on the other hand of being liable to come into undesirable contact with naturally magnetic surfaces in the course of the transfer operation.

SUMMARY OF THE INVENTION

Accordingly it is an object of the present invention to provide a magnetized device which responds better to the necessities of practice than magnetic means directed to the same purpose, previously known, particularly in that it is provided with insulation which avoids any false manoeuvre and return means which prevent accidental contact of the magnetic means with magnetic surfaces during the transfer of the beads of magnetic gel.

According to the present invention there is provided a magnetized device for withdrawing magnetic gel beads or the like from a biological fluid and for transferring them to an immunoenzymatic assay medium, of the type comprising a magnetizable rod, which device is characterized in that it comprises:

a box or housing of insulating material, particularly of plastic material, in which is formed an orifice traversing the whole height of the said housing; a rod housed in said traversing orifice which constitutes a track for guiding said rod, which rod is formed from a lower portion and an upper portion, the lower portion of the rod being constructed of non-magnetic material, a stop washer fixed to the lower surface of the housing, at the outlet of the above said traversing orifice, a spring mounted between a stop washer fixed in the vicinity of the upper end of the rod and specifically in the vicinity of the end of the upper portion, of non-magnetic material, of said rod, and said upper surface of the housing.

According to an advantageous embodiment of the magnetized device according to the invention, the housing of insulating material contains a magnet.

According to another advantageous embodiment of the magnetized device according to the invention, the upper portion, of non-magnetic material, of the rod, is fitted into the lower portion, of magnetic material, of said rod and held in the latter by means of a catch or the like.

According to another advantageous embodiment of the magnetized device according to the invention, the housing is constructed in the form of an insulating handle for said device.

According to another advantageous embodiment of the magnetized device according to the invention, the traversing guide orifice of said rod is excentric with respect to the longitudinal axis of the housing.

According to another aspect of the present invention there is provided an assembly or "kit" ready for use for carrying out immunoenzymatic assays, characterized in that it comprises:

a receptacle containing a suitable amount of magnetic gel beads coupled with an antigen or a specific antibody, a magnetized device such as defined in the foregoing, a culture dish, such as particularly a Petri dish, whose lower surface is provided externally with a powerful magnet, a receptacle containing a suitable amount of culture medium for the culture of pathogenic germs to be assayed, designed to be introduced into said culture dish, a receptacle containing a suitable amount of an antibody or a pathogenic antigerm specific antigen to be detected, designed to be introduced onto said culture medium, a receptacle containing a suitable amount of agents for lysing cultures of pathogenic germs developed in said culture dish, a receptacle containing a suitable amount of buffered physiological wash-water for washing magnetic gel beads fixed to the rod of the above noted magnetized device.

Besides the foregoing features, the invention comprises still other features, which will emerge from the description which follows.

The invention is directed more particularly at magnetized devices according to the foregoing features and immunoenzymatic assay assemblies including such devices.

BRIEF DESCRIPTION OF THE DRAWING

The invention will be better understood by means of the additional description which follows, which refers to the accompanying drawing in which:

FIG. 1 is a front view of the magnetized device according to the invention, brought back into transfer position for the magnetic gel beads which are fixed to the magnetized rod, FIG. 2 is a top view of the device of FIG. 1 and FIG. 3 is a front view of the device of FIG. 1 in the position of detaching the beads onto a suitable assay medium.

It must be well understood, however, that this drawing and the corresponding descriptive portions, are given purely by way of illustration of the object of the invention, of which they do not constitute in any way a limitation.

DESCRIPTION OF PREFERRED EMBODIMENTS

The magnetic device shown in FIGS. 1 to 3, comprises a housing 1 in which is formed a traversing orifice 2 which extends over the totality of the height of the housing 1. Although the emplacement of the traversing orifice may be anywhere, nonetheless, for reasons of convenience, to the extent that the housing, which is constructed of an insulating material, is used as a handle for gripping the device according to the invention, it is preferred that the traversing orifice 2 should be eccentric with respect to the longitudinal axis of the housing.

A rod, denoted generally by the reference 3, whose diameter is substantially equal to that of the traversing orifice 2, is mounted in the traversing orifice 2, so as to be slidable in the latter. This rod 3 comprises a lower portion 4 of magnetizable material and an upper portion 5 of non-magnetic material; the upper portion 5 of the rod 3 is nested in the upper end of the lower portion 4, in which it is fixed in position by a catch 6 or by any other suitable fastening system, such as, for example, a bayonet system.

The spring 7 is mounted on the rod 3, between a stop washer 8 fixed in the vicinity of the upper end 10 of the rod 3, and the upper surface 12 of the housing 1. A stop washer 9 is fixed to the outlet of the traversing orifice 2, on the lower surface 11 of the housing 1. The housing 1 contains a magnet 13.

The operation of the magnetized device according to the invention is as follows: pressure exerted on the upper end 10 of the rod 3 causes the sliding of rod 3 downwards, into the traversing orifice 2 formed in the housing 1, the travel of the rod 3 being limited by the spring 7 and by the concommittant compression of the latter between the stop 8 and the upper surface 12 of the housing 1 (cf. FIG. 3). The release of the thrust exerted on the upper end 10 of the rod 3 causes the recall of the rod 3 by the spring 7, into the position shown in FIG. 1, in which the portion 4 of the rod is magnetized by the magnet 13 in the housing 1.

In its application to assay processes, the magnetized device according to the invention is placed above a container holding an incubation medium comprising a biological fluid and magnetic gel beads coupled to a suitable protein to permit the carrying out of an immuno-enzymatic assay; pressure of the finger exerted by an operator on the upper end 10 of the rod 3, places in contact the magnetizable lower portion 4 of the rod 3 with the medium, which attracts the magnetic gel beads which are fixed thereto. Release of the pressure exerted on the upper end 10 of the rod 3, causes the rod 3 to be brought back into the position shown in FIG. 1, and the placing of the lower portion 4 of the rod 3 out of contact with the medium. The magnetic gel beads fixed to the portion 4 of the rod 3 are transported whilst the device is in the position shown in FIG. 1, to a recipient containing suitable assay medium. Further pressure is then exerted on the upper end 10 of the rod 3 by the operator to place the lower portion 4 of the rod 3 in contact with the assay medium which is contained in a suitable container provided externally with a magnet of which the attraction force detaches the magnetic gel beads from the portion 4 on the rod 3 making them fall onto the assay medium.

The pressure exerted on the end 10 of the rod 3 is then released, which causes the return of the rod 3 into the resting position (shown in FIG. 1), the magnetized device according to the invention being ready for a further operation.

The magnetized device according to the invention is perfectly isolated due to the arrangement of the housing 1 and the construction of the rod 3 in two portions of which the upper portion is non-magnetic. In addition, any accidental contact of the magnetized portion of the rod with the magnetized surfaces is prevented to a large extent by the return of the rod 3 into upper position during its transfer from the container containing the incubating medium to the container containing the assay medium.

As will emerge from the foregoing, the invention is in no way limited to those of its embodiments and types of application which have just been described more explicitly; it encompasses on the contrary all modifications which may come to the spirit of the technician in the art, without departing from the scope, nor the framework, of the present invention.

We claim:

1. A magnetic device for withdrawing magnetic gel beads or the like from a biological fluid and transferring the same into an immunoenzymatic assay medium, comprising in combination:
   a housing of non-magnetic material which is constructed in the form of an insulating handle of said device and in which is formed a traversing orifice over its entire height, said traversing orifice being eccentric with respect to the vertical axis of the housing,
   a magnetic eccentrically housed in said housing with respect to the vertical axis of this latter,
   a rod housed in said eccentric traversing orifice, said orifice constituting a guide track for said rod, wherein said rod comprises an upper portion of non-magnetic material and a lower portion of magnetizable material, the latter having two limiting positions, namely a retracted position, in which the magnetizable portion is under the magnetic influence of said magnet so as to exert a magnetic force, and a projected position, in which the magnetizable portion is beyond the magnetic influence of the magnet, and detachable fixing means for fastening said lower magnetizable portion of the rod to said upper non-magnetic portion of said rod such that said lower magnetizable portion is detachable from said upper non-magnetic portion of said rod,
   manually operable means for bringing said lower magnetizable portion of said rod into said projected position, and
   spring means for maintaining said lower magnetizable portion of said rod in said retracted position and to move said rod back into said retracted position after releasing said manually operable means.

2. An assembly for use in performing immunoenzymatic assays, comprising:
   a receptacle containing a suitable amount of magnetic gel beads or the like coupled with an antigen or a specific antibody, a magnetic device for withdrawing said magnetic gel beads from said receptacle and transferring the same into an immunoenzymatic assay medium, a culture dish having a lower surface provided externally with a high power magnet, a receptacle containing a suitable amount of culture medium for the culture of pathogenic germs to be assayed, to be introduced into said culture dish, a receptacle containing a suitable amount of an antibody or a specific pathogenic anti-germ antigen to be detected, for introduction onto said culture medium, a receptacle containing a suitable amount of lysis agents of the pathogenic germ cultures developed in said culture dish, and a receptacle containing a suitable amount of buffered physiological wash water wherein said magnet device comprises in combination:

a housing of non-magnetic material which is constructed in the form of an insulating handle of said device and in which is formed a traversing orifice over its entire height, said traversing orifice being eccentric with respect to a vertical axis of the housing, a magnet eccentrically housed in said housing with respect to the vertical axis of the latter, a rod housed in said eccentric traversing orifice, said orifice constituting a guide track for said rod, wherein said rod comprises an upper portion of non-magnetic material and a lower portion of magnetizable material, the latter having two limiting positions, namely a retracted position, in which the magnetizable portion is under the magnetic influence of said magnet, and a projected position, in which the magnetizable portion is beyond the magnetic influence of the magnet, and means for detachably fastening said said lower magnetizable portion of the rod to said upper non-magnetic portion of said rod such that said lower magnetizable portion is detachable from said upper non-magnetic portion of said rod, manually operable means for bringing said lower magnetizable portion of said rod into said projected position, and spring means for maintaining said lower magnetizable portion of said rod into said retracted position and to move said rod back into said retracted position after releasing said manually operable means.

* * * * *